US00PP13471P3

(12) United States Plant Patent
Olesen et al.

(10) Patent No.: US PP13,471 P3
(45) Date of Patent: Jan. 14, 2003

(54) MINIATURE ROSE PLANT NAMED 'POULGO005'

(76) Inventors: L. Pernille Olesen, Hillerødvejen 49, DK-3480, Fredensborg (DK); Mogens N. Olesen, Hillerødvejen 49, Dk-3480, Fredensborg (DK)

( * ) Notice: Subject to any disclaimer, the term of this patent is extended or adjusted under 35 U.S.C. 154(b) by 21 days.

(21) Appl. No.: 09/776,450

(22) Filed: Feb. 2, 2001

(65) Prior Publication Data

US 2002/0148010 P1 Oct. 10, 2002

(51) Int. Cl.[7] ..... A01H 5/00
(52) U.S. Cl. ..... Plt./118

(58) Field of Search ..... Plt./118

(56) References Cited

PUBLICATIONS

UPOV–ROM GTITM Computer Database, 2001/06, GTI Jouve Retrieval Software, citation for 'POULgo005'.*

* cited by examiner

*Primary Examiner*—Bruce R. Campell
*Assistant Examiner*—Susan B. McCormick

(57) ABSTRACT

A new miniature rose plant which has abundant, yellow flowers and attractive foliage. This new and distinct variety has shown to be uniform and stable in the resulting generations from asexual propagation.

1 Drawing Sheet

SUMMARY OF THE INVENTION

Classification:

*Botanical.*—*Rosa hybrida* 'POULgo005'.

*Commercial.*—Miniature.

The present invention constitutes a new and distinct variety of miniature rose plant which originated from a controlled crossing between 'POULgelb', described and illustrated in U.S. Plant Pat. No. 9,401, issued on Dec. 19, 1995 and an unnamed and unpatented seedling. The two parents were crossed during the summer of 1995 and the resulting seeds were planted in a controlled environment in Fredensborg, Denmark. The new variety is named 'POULgo005'.

The new rose may be distinguished from its seed parent, 'POULgelb', by the following combination of characteristics:

1. 'POULgelb' is a miniature rose, whereas 'POULgo005' is a compact floribunda rose.
2. 'POULgelb' has deeper yellow blooms than 'POULgo005'.
3. The blooms of 'POULgelb' are smaller than those of 'POULgo005'.

The new variety may be distinguished from its pollen parent, an unnamed seedling, by the following combination of characteristics:

1. 'POULgo005' is a yellow rose, where the unnamed pollen parent is pink.
2. The blooms of the unnamed pollen parent are larger than those of 'POULgo005'.

The objective of the hybridization of this rose variety was to create a new and distinct variety for garden use with unique qualities, such as:

1. Uniform and abundant flowers;
2. Vigorous, but compact growth when propagated by cuttings;
3. Disease resistance;
4. A miniature rose suitable for use in hanging basket containers in the nursery industry.

This combination of qualities is not present in previously available commercial cultivars of this type and distinguish 'POULgo005' from all other varieties of which we are aware.

As part of their rose development program, L. Pernille Olesen and Mogens N. Olesen germinated the seeds from the aforementioned hybridization during winter of 1995 and conducted evaluations on the resulting seedlings in a controlled environment in Fredensborg, Denmark.

'POULgo005' was selected in the spring of 1996 by the inventors as a single plant from the progeny of the aforementioned hybridization.

Asexual reproduction of 'POULgo005' by traditional budding and rooted cuttings was first done by L. Pernille and Mogens N. Olesen in their nursery in Fredensborg, Denmark in July 1996. This initial and other subsequent asexual propagations conducted in controlled environments have demonstrated that the characteristics of 'POULgo005' are true to type and are transmitted from one generation to the next.

BRIEF DESCRIPTION OF THE DRAWING

The accompanying color illustration shows as true as is reasonably possible to obtain in color photographs of this type the variety rose 'POULgo005'.

Specifically illustrated in SHEET 1 is a plant of 'POULgo005' growing in a 20-cm hanging basket.

DETAILED DESCRIPTION OF THE VARIETY

The following is a description of 'POULgo005', as observed in its growth during trials at the testing station Prüfstelle Rethmar under the testing authority Bundessortenamtin in Hannover, Germany and at the inventor's nursery in Fredensborg, Denmark. Color references are made using The Royal Horticultural Society (London, England) Colour Chart, 1995, except where common terms of color are used.

For a comparison, several physical characteristics of the rose variety 'POULgelb', a rose variety from the same inventors described and illustrated in U.S. Plant Pat. No. 9,401 and issued on Dec. 19, 1995 are compared to 'POULgo005' in Chart 1.

CHART 1

| | 'POULgo005' | 'POULgelb' |
|---|---|---|
| Color of open flower, outer side, middle zone. | Yellow Group 6D | Yellow Group 13C |
| Petalage | Single | Double |
| Average Bloom Diameter | 'Small' | 'Small' |

Parents:

*Seed parent.*—'POULgelb'.

*Pollen parent.*—An unnamed seedling.

FLOWER AND FLOWER BUD

Blooming habit: Continuous.

Flower bud:

*Size.*—18 mm in length from base of receptacle to end of bud. Diameter is 25 mm.

*Bud form.*—Long, pointed ovoid.

*Bud color.*—As sepals unfold, Yellow Group 2C; Yellow Group 7C at ¼ opening.

*Sepals.*—Shape: Sepal apex is cirrose; base is flat at union with peduncle. Length: 15 to 35 mm. Width: 8 to 9 mm. Color: Upper surface is Yellow-Green Group 144 B and C. Lower surface is Yellow-Green Group 144 B and C. Appendages: Weak foliaceous appendages on 4 of the five sepals. Pubescence: Moderate. Stipitate Glands: Stipitate glands present on sepal margins.

*Receptacle.*—Surface: Glaucous. Shape: Funnel-shaped. Size: 5 mm (h)×6 mm (w). Color: Green Group 144B, with some anthocyanin intonation of Greyed-Purple Group 183D.

*Peduncle.*—Surface: Many stipitate glands and fine white hairs present. Length: 28 to 32 mm. Color: Yellow-Green Group 144B. Strength: Somewhat strong. Anthocyanin: Greyed-Purple Group 183D.

Borne.—2 to 3 buds per stem.

Flower bloom:

*Fragrance.*—Light, fresh scent.

*Duration.*—As a pot plant, flowers last from 12 to 15 days.

*Size.*—Small. Average flower diameter is between 40 to 45 mm when open.

*Form.*—Shape of flower when viewed from the side: Upon opening, upper part: Flattened convex. Upon opening, lower part: Flattened convex. After opening, upper part: Flattened convex. After opening, lower part: Concave. Petalage: Very double. Average range: 85 to 90 petals, with 10 to 15 petaloids.

Color

Petals:

*Inner side.*—Middle zone: Yellow Group 7B. Marginal zone: Yellow Group 7B. Basal petal spot: None observed.

*Outer side.*—Middle zone: Yellow Group 7B. Marginal zone: Yellow Group 7B. Basal petal spot: None observed.

General tonality: On open flower, Yellow Group 7B. No change in the general tonality at the end of the 10th day.

Petals:

*Size.*—15 mm (l)×9 mm (w).

*Petal reflex.*—Slight.

*Shape.*—Obovate. Apex is entire with occasional notch in center and base is acute.

*Petaloids.*—4 to 6. Petaloids are 6 mm long and 3 to 4 mm wide. Petaloid coloration is Yellow Group 7B on both upper and lower surfaces.

*Thickness.*—Thin.

*Arrangement.*—Imbricated.

*Edge.*—Entire.

Reproductive organs:

*Filaments.*—Color: Yellow Group 12A. Length: 4 mm.

*Pistils.*—Length: 8 mm. Quantity: 20 to 22.

*Pollen.*—Color: Yellow-Orange Group 14A. Quantity: Scant.

*Anthers.*—Length: 2 mm. Color: Yellow-Orange Group 14D. Quantity: 32 to 34.

*Stigmas.*—Height: Stigmas are even in height relative to anthers. Color: Greyed-Green Group 196D.

*Styles.*—Color: Red Group 47A. Length: 5 mm.

*Hips.*—None observed.

*Seed production.*—None observed to date.

PLANT

Plant growth: Compact, spreading growth. Average height of the plant is 35 cm; the average width is 30 cm.

Stems:

*Color.*—Young wood: Yellow-Green Group 144B. Older wood: Yellow-Green Group 144A and B.

*Thorns.*—Incidence: 5 to 8 thorns per 10 cm of stem. Size: Average length is 3 mm. Color: Greyed-Yellow Group 160C. Shape: Linear.

*Surface.*—Older wood: Smooth. Young wood: Smooth.

*Size.*—Length: 18 cm. Diameter: 3 to 4 mm.

Plant foliage:

*Number of leaflets on normal leaves in middle of a stem.*—5.

*Leaf size.*—60 mm (l) by 40 mm (w).

*Quantity.*—Average.

*Glossiness.*—Upper side weak glossiness.

*Color.*—Mature foliage: Upper Leaflet Surface: Green Group 137A. Lower Leaflet Surface: Yellow-Green Group 147B. Juvenile foliage: Upper Leaflet Surface: Yellow-Green Group 146A. Lower Leaflet Surface: Yellow-Green Group 146C. Anthocyanin intonation: Greyed-Red Group 185A on margins of upper leaflet surface, all of lower surface, petiole, rachis, and stipule.

Plant leaflets:

*Stipule.*—Size: 10 mm (l)×4 mm (w). Color: Yellow-Green Group 144B and C. Anthocyanin: Greyed-Red Group 183C. Stipitate Glands: On edges of stipules.

*Petiole.*—Length: 7 mm. Color: Yellow-Green Group 144B. Underneath: Yellow-Green Group 144B. Stipitate glands and occasionally a single, small thorn. Margins: Yellow-Green Group 144A. Anthocyanin: Greyed-Red Group 183C.

*Rachis.*—Color: Yellow-Green Group 144B. Underneath: Yellow-Green Group 144B. Stipitate glands and occasionally a single, small thorn. Margins: Yellow-Green Group 144A. Stipitate glands present. Anthocyanin: Greyed-Red Group 183C.

*Leaflet.*—Edge: Finely serrated. Shape: Ovate. Surface: Moderately glossy. Texture: Leathery. Arrangement: Odd pinnate. Venation: Reticulate.

Disease resistance: Above average resistance to mildew, rust, black spot, and Botrytis under normal growing conditions in Jackson County, Oreg.

Cold hardiness: The variety 'POULgo005' has been found to be resistant to damage from cold in USDA Zone 7.

We claim:

1. A new and distinct variety of rose plant of the miniature rose class, substantially as herein illustrated and described as a distinct and novel rose variety due to its abundant yellow flowers, procumbent to arching habit, disease resistance, and extended period of bloom.

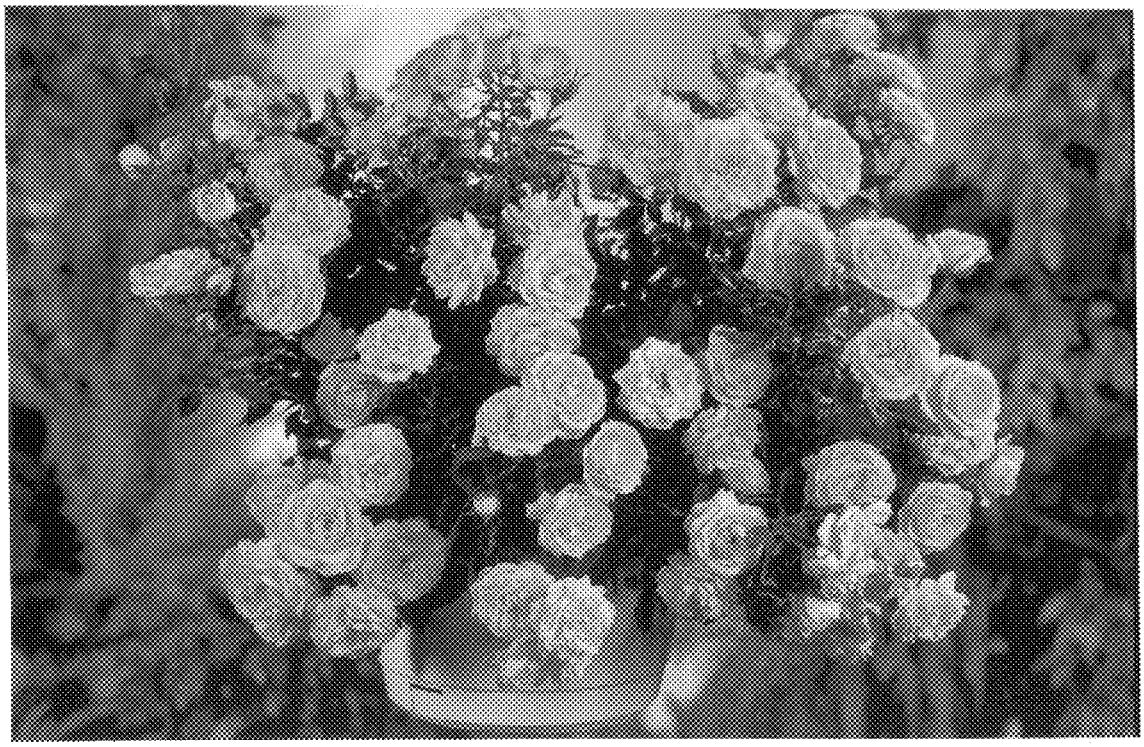

* * * * *